(12) United States Patent
Uckun (10) Patent No.: US 7,186,736 B1
(45) Date of Patent: Mar. 6, 2007

(54) NNI FOR TREATMENT OF MULTI-DRUG RESISTANT HIV

(75) Inventor: Fatih M. Uckun, White Bear Lake, MN (US)

(73) Assignee: Parker Hughes Institute, Roseville, MN (US)

( * ) Notice: Subject to any disclaimer, the term of this patent is extended or adjusted under 35 U.S.C. 154(b) by 668 days.

(21) Appl. No.: 09/272,821

(22) Filed: Mar. 20, 1999

(51) Int. Cl.
*A61K 31/44* (2006.01)
*A61K 31/17* (2006.01)

(52) U.S. Cl. ............... 514/352; 514/580; 514/585

(58) Field of Classification Search .......... 514/247, 514/255, 332, 352, 580, 585
See application file for complete search history.

(56) References Cited

U.S. PATENT DOCUMENTS

| | | | |
|---|---|---|---|
| 4,724,232 A | * | 2/1988 | Rideout et al. ............... 514/50 |
| 5,593,993 A | | 1/1997 | Morin, Jr. et al. .......... 514/247 |
| 5,658,907 A | | 8/1997 | Morin, Jr. et al. .......... 514/247 |
| 5,686,428 A | | 11/1997 | Eriksson et al. .............. 514/50 |
| 5,714,503 A | | 2/1998 | Morin, Jr. et al. .......... 514/332 |
| 5,786,462 A | | 7/1998 | Schneider et al. ......... 536/23.1 |

FOREIGN PATENT DOCUMENTS

| | | | |
|---|---|---|---|
| WO | WO 93/03022 | * | 2/1993 |
| WO | WO 99/47501 | | 9/1999 |

OTHER PUBLICATIONS

Ahgren, C. et al., "The PETT series, a new class of potent non-nucleoside inhibitors of human immunodeficiency virus Type 1 reverse transcriptase", *Antimicrob. Agents Chemother.*, vol. 39, No. 6, pp. 1329-1335 (Jun. 1995).

Artico, M. et al., "3,4-Dihydro-2-alkoxy-6-benzyl-4-oxopyrimidines (DABOs): a new class of specific inhibitors of human immunodeficiency virus Type 1", *Antiviral Chem. Chemother*, vol. 4, No. 6, pp. 361-368 (1993).

Baba, M. et al., "Highly potent and selective inhibition of HIV-1 replication by 6-phenylthiouracil derivatives", *Antiviral Res.*, vol. 17, No. 4, pp. 245-264 (Apr. 1992).

Balzarini, J. et al., "2',5'-Bis-O-(*tert*-butyldimethylsilyl)-3'-spiro-5"-(4"-amino-1",2"-oxathiole-2",2"-dioxide)pyrimidine (TSAO) nucleoside analogues: Highly selective inhibitors of human immunodeficiency virus type 1 that are targeted at the viral reverse transcriptase", *Proc. Natl. Acad. Sci. USA*, vol. 89, No. 10, pp. 4392-4396 (May 1992).

Barlett, P.A., et al., "Caveat: A program to facilitate the structure-derived design of biologically active molecules", *Molecular Recognition in: Chemical and Biochemical Problems*, Special Publication No. 78, pp. 182-196 (Apr. 1989).

Bell, F.W. et al., "Phenethylthiazolethiourea (PETT) compounds, a new class of HIV-1 reverse transcriptase ihibitors. 1. Synthesis and basic structure-activity relationship studies of PETT analogs", *J. Med. Chem.*, vol. 38, No. 25, 4929-4936 (1995).

Blaney, J.M. et al., "A good ligand is hard to find: Automated docking methods", *Perspectives in Drug Discovery and Design*, vol. 1, No. 2, pp. 301-319 (Dec. 1993)).

Böhm, H., "The computer program LUDI: A new method for the de novo design of enzyme inhibitors", *Journal of Computer-Aided Molecular Design*, vol. 6, No. 1, pp. 61-78 (Feb. 1992).

Böhm, H., "LUDI: rule-based automatic design of new subsituents for enzyme inhibitor leads", *Journal of Computer-Aided Molecular Design*, vol. 6, No. 6, pp. 593-606 (Dec. 1992).

Böhm, H., "The development of a simple empirical scoring function to estimate the binding constant for a protein-ligand complex of known three-dimensional structure", *Journal of Computer-Aided Molecular Design*, vol. 8, No. 3, pp. 243-256 (Jun. 1994).

Bosworth, N., et al., "Scintillation proximity assay", *Nature*, vol. 341, No. 6238, pp. 167-168 (Sep. 14, 1989).

Burkert, U. et al., "Methods for the computation of molecular geometry", *Molecular Mechanics*, ACS Monograph 177, American Chemical Society, Chapter 3, pp. 59-78 (1982).

Brooks, B.R. et al., "CHARMM: A program for macromolecular energy, minimization, and dynamics calculations", *J. Comp. Chem.*, vol. 4, No. 2, pp. 187-217 (1983).

Cantrell, A.S. et al., "Phenethylthiazolylthiourea (PETT) compounds as a new class of HIV-1 reverse transcriptase inhibitors. 2. synthesis and further structure-activity relationship studies of PETT analogs", *J. Med. Chem.*, vol. 39, No. 21, pp. 4261-4274 (Oct. 1996).

Connolly, M.L., "Solvent-Accessible Surfaces of Proteins and Nucleic Acids", *Science*, vol. 221, No. 4612, pp. 709-713 (Aug. 19, 1983).

Danel, K. et al., "Synthesis and potent Anti-HIV-1 activity of novel 6-benzyluracil analogues of 1-[2-hydroxyethoxy)methyl]-6-(phenylthio)thymine", *J. Med. Chem.*, vol. 39, No. 12, pp. 2427-2431 (1996).

Danel, K. et al., "Anti-HIV active napthyl analogues of HEPT and DABO", *Acta Chemica Scandinavica*, vol. 51, No. 3(S), pp. 426-430 (Mar. 1997).

Danel, K. et al., "Synthesis and Anti-HIV-1 activity of novel 2,3-dihydro-7*H*-thiazolo[3,2-α] pyrimidin-7-ones", *J. Med. Chem.*, vol. 41, No. 2, pp. 191-198 (1998).

Das, K. et al., "Crystal Structures of 8-Cl and 9-Cl TIBO Complexed with Wild-type HIV-1 RT and 8-Cl TIBO Complexed with the Tyr181Cys HIV-1 RT Drug-resistant Mutant", *J. Mol. Biol.*, vol. 264, No. 5, pp. 1085-1100 (Dec. 20, 1996).

De Clercq, E., "HIV Inhibitors Targeted at the Reverse Transcriptase", *AIDS Research and Human Retroviruses*, vol. 8, No. 2, pp. 119-134 (Feb. 1992).

Ding, J., "Structure of HIV-1 RT/TIBO R 86183 complex reveals similarity in the binding of diverse nonnucleoside inhibitors", *Nat. Struct. Biol.*, vol. 2, No. 5, pp. 407-415 (May 1995).

Erice, A. et al., "Anti-Human Immunodeficiency Virus Type 1 Activity of an Anti-CD4 Immunoconjugate Containing Pokeweed Antiviral Protein", *Antimicrob. Agents Chemother.*, vol. 37, No. 4, pp. 835-838 (Apr. 1993).

(Continued)

Primary Examiner—Shengjun Wang
(74) Attorney, Agent, or Firm—Merchant & Gould PC (57) ABSTRACT

The present invention is directed to compounds and methods suitable for the treatment of HIV infection.

22 Claims, 1 Drawing Sheet

OTHER PUBLICATIONS

Esnouf, R.M. et al., "Unique features in the structure of the complex between HIV-1 reverse transcriptase and the bis(heteroaryl)piperazine (BHAP) U-90152 explain resistance mutations for this nonnucleoside inhibitor", *Proc. Natl. Acad. Sci. U.S.A.*, vol. 94, No. 8, pp. 3984-3989 (Apr. 15, 1997).

Goodsell, D.S. et al., "Automated Docking of Substrates to Proteins by Simulated Annealing", PROTEINS: *Structure, Function, and Genetics*, vol. 8, pp. 195-202 (1990).

Greene, W.C., "The molecular biology of human immunodeficiency virus type 1 infection", *New England Journal of Medicine*, vol. 324, No. 5, pp. 308-317 (Jan. 31, 1991).

Heinisch, G. et al., "The inhibitory activity of diazinyl-substituted thiourea derivatives on human immunodeficiency virus type 1 reverse transcriptase", *Antiviral Chemistry & Chemotherapy*, vol. 8, No. 5, pp. 443-446 (Sep. 1997).

Hopkins, A.L. et al., "Complexes of HIV-1 Reverse Transcriptase with Inhibitors of the HEPT Series Reveal Conformational Changes Relevant to the Design of Potent Non-Nucleoside Inhibitors", *J. Med. Chem.*, vol. 39, No. 8, pp. 1589-1600 (1996).

Hsiou, Y. et al., "Structures of Tyr188Leu Mutant and Wild-type HIV-1 Reverse Transcriptase Complexed with the Non-nucleoside Inhibitor HBY 097: Inhibitor Flexibility is a Useful Design Feature for Reducing Drug Resistance", *J. Mol. Biol.*, vol. 284, No. 2, pp. 313-323 (Nov. 27, 1998).

Huang, H. et al., "Structure of a Covalently Trapped Catalytic Complex of HIV-1 Reverse Transcriptase: Implications for Drug Resistance", *Science*, vol. 282, No. 5394, pp. 1669-1675 (Nov. 27, 1998).

Jones, T.A. et al., "Improved Methods for Building Protein Models in Electron Density Maps and the Location of Errors in these Models", *Acta Cryst*, vol. A47, Part 2, pp. 110-119 (Mar. 1, 1991).

Kohlstaedt, L.A. et al., "Crystal Structure at 3.5 Å Resolution of HIV-1 Reverse Transcriptase Complexed with an Inhibitor", *Science*, vol. 256, pp. 1783-1790 (Jun. 26, 1992).

Kroeger Smith, M.B. et al., Molecular modeling studies of HIV-1 reverse transcriptase nonnucleoside inhibitors: Total energy of complexation as a predictor of drug placement and activity, *Protein Science*, vol. 4, pp. 2203-2222 (1995).

Kuntz, I.D. et al., "A Geometric Approach to Macromolecule-Ligand Interactions", *J. Mol. Biol.*, vol. 161, No. 2, pp. 269-288 (Oct. 25, 1982).

Larder, B.A. et al., "Convergent combination therapy can select viable multidrug-resistant HIV-1 *in vitro*", *Nature*, vol. 365, No. 6445, pp. 451-453 (Sep. 30, 1993).

Luty, B.A. et al., "A Molecular Mechanics/Grid Method for Evaluation of Ligand-Receptor Interactions", *J. Comp. Chem.*, vol. 16, No. 4, pp. 454-464 (Apr. 1995).

Mai, A. et al., "Synthesis and Anti HIV-1 Activity of Thio Analogues of Dihydroalkoxybenzyloxopyrimidines", *J. Med. Chem.*, vol. 38, No. 17, 3258-3263 (Aug. 18, 1995).

Mai, A. et al., "Dihydro(alkylthio)(naphthylmethyl) oxopyrimidines: Novel Non-Nucleoside Reverse Transcriptase Inhibitors of the S-DABO Series", *J. Med. Chem.*, vol. 40, No. 10, pp. 1447-1454 (May 9, 1997).

Mao, C. et al., "Structure-based design of N-[2-(1-piperidinylethyl)]-N'-[2-(5-bromopyridyl)]-thiourea and N-[2-(1-piperazinylethyl)]-N'-[2-(5-bromopyridyl)]-thiourea as potent nonnucleoside inhibitors of HIV-1 reverse transcriptase", *Bioorg. Med. Chem. Lett.*, vol. 8, pp. 2213-2218 (1998).

Mao, C. et al., "Rational Design of N-[2-(2,5-Dimethoxyphenylethyl)]-N'-[2-(5-Bromopyridyl)]-Thiourea (HI-236) as a Potent Non-Nucleoside Inhibitor of Drug-Resistant Human Immunodeficiency Virus", *Bioorganic & Medicinal Chemistry Letters*, vol. 9, No. 11, pp. 1593-1598 (Jun. 7, 1999).

Marshall, G.R. "Computer-Aided Drug Design", *Ann. Rev. Pharmacol. Toxicol.*, vol. 27, pp. 193-213 (1987).

Martin, Y.C., "3D Database Searching in Drug Design", *J. Med. Chem.*, vol. 35, No. 12, pp. 2145-2154 (Jun. 12, 1992).

Massa, S. et al., "Synthesis and antiviral activity of new 3,4-dihydro-2-alkoxy-6-benzyl-4-oxopyrimidines (DABOs), specific inhibitors of human immunodeficiency virus type 1", *Antiviral Chem. Chemother*, vol. 6, No. 1, pp. 1-8 (Jan. 1995).

Miles, S., "Introduction", *J. Acquir. Immune Defic. Syndr. Hum. Retrovirol*, vol. 16, Suppl. 1, pp. S1-S2 (1997).

Mitsuya, H. et al., "Molecular Targets for AIDS Therapy", *Science*, vol. 249, pp. 1533-1544 (Sep. 28, 1990).

Nishibata, Y. et al., "Automatic Creation of Drug Candidate Structures Based on Receptor Structure. Starting Point for Artificial Lead Generation", *Tetrahedron*, vol. 47, No. 43, pp. 8985-8990 (Nov. 4, 1991).

Nunberg, J.H. et al., "Viral Resistance to Human Immunodeficiency Virus Type 1-Specific Pyridinone Reverse Transcripase Inhibitors", *J. Virol.*, vol. 65, No. 9, pp. 4887-4892 (Sep. 1991).

Pauwels, R. et al., "Potent and selective inhibition of HIV-1 replication *in vitro* by a novel series of TIBO derivatives", *Nature*, vol. 343, No. 6257, pp. 470-474 (Feb. 1, 1990).

Pontikis, R. et al., "Synthesis and Anti-HIV Activity of Novel N-1 Side Chain-Modified Analogs of 1-[(2-Hydroxyethoxy)methyl]-6-(phenylthio)thymine (HEPT)", *J. Med. Chem.*, vol. 40, No. 12, pp. 1845-1854 (1997).

Remington's Pharmaceutical Sciences, Chapter 43, 14th Ed., Mack Publishing Co., Easton, PA 18042, USA, "Topical Drugs", pp. 763-786, date unknown.

Ren, J. et al., "High resolution structures of HIV-1 RT from four RT-inhibitor complexes", *Nat. Struct. Biol.*, vol. 2, No. 4, pp. 293-302 (Apr. 1995).

Ren, J. et al., "The structure of HIV-1 reverse transcriptase complexed with 9-chloro-TIBO: lessons for inhibitor design", *Structure*, vol. 3, No. 9, pp. 915-926 (1995).

Richman, D. et al., "Human immunodeficiency virus type 1 mutants resistant to nonnucleoside inhibitors of reverse transcriptase arise in tissue culture", *Proc. Natl. Acad. Sci. USA*, vol. 88, No. 24, pp. 11241-11245 (Dec. 15, 1991).

Romero, D.L. et al., "Bis(heteroaryl)piperazine (BHAP) Reverse Transcriptase Inhibitors: Structure-Activity Relationships of Novel Substituted Indole Analogues and the Identification of 1-[(5-Methanesulfonamido-1H-indol-2-yl)-carbonyl]-4-[3-[(1-methylethyl)amino]-pyridinyl]piperazine Monomethanesulfonate (U-90152S), a Second-Generation Clinical Candidate", *J. Med. Chem.*, vol. 36, No. 10, pp. 1505-1508 (1993).

Sahlberg, C. et al., "Synthesis and Anti-HIV Activities of Urea-PETT Analogs Belonging to a New Class of Potent Non-Nucleoside HIV-1 Reverse Transcriptase Ihibitors", *Bioorganic & Medicinal Chemistry Letters*, vol. 8, No. 12, pp. 1511-1516 (Jun. 16, 1998).

Sudbeck, E.A. et al., "Structure-Based Design of Novel Dihydroalkoxybenzyloxopyrimidine Derivatives as Potent Non-nucleoside Inhibitors of the Human Immunodeficiency Virus Reverse Transcriptase", *Antimicrob. Agents Chemother*, vol. 42, No. 12, pp. 3225-3233 (Dec. 1998).

Tanaka, H. et al., "A New Class of HIV-1-Specific 6-Substituted Acyclouridine Derivatives: Synthesis and Anti-HIV-1 Activity of 5- or 6-Substituted Analogues of 1-[(2-Hydroxyethoxy)methyl]-6-(phenylthio)thymine (HEPT)" *J. Med. Chem.*, vol. 34, No. 1, pp. 349-357 (1991).

Tantillo, C. et al., "Locations of Anti-AIDS Drug Binding Sites and Resistance Mutations in the Three-dimensional Structure of HIV-1 Reverse Transcriptase", *J. Mol. Biol.*, vol. 243, No. 3, pp. 369-387 (Oct, 28, 1994).

Tramontano, E. et al., "Characterization of the anti-HIV-1 activity of 3,4-dihydro-2-alkoxy-6-benzyl-4-oxopyrimidines (DABOs), new non-nucleoside reverse transcriptase inhibitors", *Microbiologica*, vol. 17, pp. 269-279 (1994).

Uckun, F.M. et al., "TXU (Anti-CD7)-Pokeweed Antiviral Protein as a Potent Inhibitor of Human Immunodeficiency Virus", *Antimicrob. Agents and Chemother.*, vol. 42, No. 2, pp. 383-388 (Feb. 1998).

Vig, R. et al., "Rational Design and Synthesis of Phenethyl-5-bromopyridyl Thiourea Derivatives as Potent Non-nucleoside Inhibitors of HIV Reverse Transcriptase", *Bioorg. Med. Chem.*, vol. 6, pp. 1789-1797 (1998).

Vig, R. et al., "5-alkyl-2-[(methylthiomethyl)thio]-6-(benzyl)-pyrimidin-4-(1H)-ones as potent non-nucleoside reverse transcriptase inhibitors of S-DABO series", *Bioorg. & Med. Chem. Lett.,* vol. 8, pp. 1461-1466 (1998).

Weiner, S.J. et al., "A New Force Field for Molecular Mechanical Simulation of Nucleic Acids and Proteins", *J. Am. Chem. Soc.,* vol. 106, pp. 765-784 (1984).

Zarling, J.M. et al., "Inhibition of HIV replication by pokeweed antiviral protein targeted to CD4$^+$ cells by monoclonal antibodies", *Nature,* vol. 347, No. 6288, pp. 92-95 (Sep. 6, 1990).

Zhang, H. et al., Inhibition of human immunodeficiency virus type 1 wild-type and mutant reverse transcriptases by the phenyl ethyl thiazolyl thiourea derivatives trovirdine and MSC-127, *Antiviral Res.,* vol. 28, No. 4, pp. 331-342 (1995).

Zhang, H. et al., "Synergistic inhibition of HIV-1 reverse transcriptase and HIV-1 replication by combining trovirdine with AZT, ddI and ddC in vitro", *Antiviral Chem. & Chemother,* vol. 7, No. 5, pp. 221-229 (1996).

* cited by examiner

FIG. 1

NNI FOR TREATMENT OF MULTI-DRUG RESISTANT HIV

FIELD OF THE INVENTION

The invention relates to inhibitors of reverse transcriptase effective against mutant strains of HIV and effective in the treatment of multi-drug resistant HIV infection.

BACKGROUND OF THE INVENTION

Agents currently used to treat HIV infections attempt to block replication of the HIV virus by blocking the reverse transcriptase or by blocking the HIV protease. Three categories of anti-retroviral agents in clinical use are nucleoside analogs (such as AZT), protease inhibitors (such as nelfinavir), and the recently introduced non-nucleoside reverse transcriptase inhibitors (NNI) such as nevirapine.

The recent development of potent combination anti-retroviral regimens have significantly improved the prognosis for persons with HIV and AIDS. Combination therapies may be a significant factor in the dramatic decrease in deaths from AIDS (death rate as well as absolute number). The most commonly used combinations include two nucleoside analogs with or without a protease inhibitor.

Nevirapine is currently the only NNI compound which has been used in combination with AZT and/or protease inhibitors for the treatment of HIV. A new series of effective drug cocktails will most likely involve other NNIs in combination with nucleoside and protease inhibitors as a triple action treatment to combat the growing problem of drug resistance encountered in single drug treatment strategies.

The high replication rate of the virus unfortunately leads to genetic variants (mutants), especially when selective pressure is introduced in the form of drug treatment. These mutants are resistant to the anti-viral agents previously administerd to the patient. Switching agents or using combination therapies may decrease or delay resistance, but because viral replication is not completely suppressed in single drug treatment or even with a two drugs combination, drug-resistant viral strains ultimately emerge. Triple drug combinations employing one (or two) nucleoside analogs and two (or one) NNI targeting RT provide a very promising therapy to overcome the drug resistance problem. RT mutant strains resistant to such a triple action drug combination would most likely not be able to function.

Dozens of mutant strains have been characterized as resistant to NNI compounds, including L1001, K103N, V106A, E138K, Y181C and Y188H. In particular, the Y181C and K103N mutants may be the most difficult to treat, because they are resistant to most of NNI compounds that have been examined.

Recently, a proposed strategy using a knock-out concentration of NNI demonstrated very promising results. The key idea in this strategy is to administer a high concentration of NNI in the very beginning stages of treatment to reduce the virus to undetectable levels in order to prevent the emergence of drug-resistant strains. The ideal NNI compound for optimal use in this strategy and in a triple action combination must meet three criteria:

1) very low cytotoxicity so it can be applied in high doses;
2) very high potency so it can completely shut down viral replication machinery before the virus has time to develop resistant mutant strains; and
3) robust anti-viral activity against current clinically observed drug resistant mutant strains.

Novel NNI designs able to reduce RT inhibition to sub-nanomolar concentrations with improved robustness against the most commonly observed mutants and preferably able to inhibit the most troublesome mutants are urgently needed.

New antiviral drugs have the following desired characteristics: (1) potent inhibition of RT; (2) minimum cytotoxicity; and (3) improved ability to inhibit known drug resistant strains of HIV. Currently, few anti-HIV agents possess all of these desired properties.

Two non-nucleoside inhibitors (NNI) of HIV RT that have been approved by the US Food and Drug Administration for licensing and sale in the United States are nevirapine (dipyridodiazepinone derivative) and delavirdine (bis(heteroaryl) piperazine (BHAP) derivative, BHAP U-90152). Other promising new non-nucleoside inhibitors (NNIs) that have been developed to inhibit HIV RT include dihydroalkoxybenzyloxopyrimidine (DABO) derivatives, 1-[(2-hydroxyethoxy)methyl]-6-(phenylthio)thymine (HEPT) derivatives, tetrahydrobenzondiazepine (TIBO), 2',5'-Bis-O-(tert-butyldimethylsilyl)-3'-spiro-5"-(4"-amino-1",2"-oxathiole-2", 2'-dioxide)pyrimidine (TSAO), oxathiin carboxanilide derivatives, quinoxaline derivatives, thiadiazole derivatives, and phenethylthiazolylthiourea (PETT) derivatives.

NNIs have been found to bind to a specific allosteric site of HIV-RT near the polymerase site and interfere with reverse transcription by altering either the conformation or mobility of RT, thereby leading to a noncompetitive inhibition of the enzyme.

A number of crystal structures of RT complexed with NNIs have been reported (including α-APA, TIBO, Nevirapine, and HEPT derivatives), and such structural information provides the basis for further derivatization of NNI aimed at maximizing binding affinity to RT. However, the number of available crystal structures of RT NNI complexes is limited.

Given the lack of structural information, alternate design procedures must be relied upon for preparing active inhibitors. One such method which provides important information about predicting inhibitor interactions is receptor-targeted molecular modeling which heavily relies on the integrated information from crystal structures. The inclusion of such modeling information in the drug design process is likely to contribute to a more efficient identification of promising non-nucleoside inhibitors of HIV RT.

In the design of novel inhibitors, it is our working hypothesis that by examining multiple crystal structures of RT-NNI complexes can one understand precisely how the NNI pocket can adjust to accomodate the binding of a particular NNI. Our composite binding pocket, unlike a single crystal structure, is able to summarize the nature and extent of the flexibility of the active site residues in the NNI binding site of RT. This allowed the de novo design of PETT compounds after positioning the compounds into the NNI active site of RT.

As described in copending U.S. patent application Ser. No. 09/040,538, two major features observed from the composite binding pocket model are previously unidentified spacious regions and polar regions at the Wing 2 portion of the binding pocket. It was postulated that the spacious or flexible regions of the binding pocket can accommodate and interact favorably with functional groups larger than a pyridyl ring at the Wing 2 region. Polar regions of the binding pocket would interact favorably with properly positioned polar groups on the inhibitor molecule, such as halogen groups.

Using the composite binding pocket model, a series of potent NNI compounds was synthesized and assayed for anti-viral activity. These compounds abrogated HIV replication in HTLVM-infected peripheral blood mononuclear cells at nanomolar concentrations ($IC_{50}[p24]$=<1 nM) without evidence of cytotoxicity ($IC_{50}[MTA]$>100 μM. Surprisingly, several compounds also demonstrated high potency against multiple drug resistant mutant strains, as discussed below and claimed herein.

SUMMARY OF THE INVENTION

Non-nucleoside inhibitors of HIV reverse transcriptase have been identified, that show particular efficacy against multiple strains of HIV, including mutant strains. The compounds of the invention were designed to interact with a composite NNI binding pocket model such that the compounds better fill spacious regions in the Wing 2 region and/or favorably interact with polar residues positioned in the Wing 2 region.

Particularly potent NNI compounds of the invention include DDE236 and DDE240, having the structural formulas shown below. DDE236 contains methoxyl groups at positions 2' and 5' of the phenyl ring, filling available space in the Wing 2 region of the composite binding pocket. DDE240 contains a fluoro group at position 2' or 6' of the phenyl ring, providing a group to interact favorably with the polar region of the Wing 2. These compounds are useful in the treatment of HIV infection, and have particular efficacy against mutant strains, making them useful in the treatment of multi-drug resistant HIV.

The compounds of the invention, including DDE 236 and DDE240 exhibit:
1) very low cytotoxicity;
2) very high potency; and
3) potent activity against clinically observed drug resistant mutant strains.

DETAILED DESCRIPTION OF THE INVENTION

Definitions:

When used herein, the following terms have the indicated meanings:

"NNI" means non-nucleoside inhibitor. In the context of the invention, non-nucleoside inhibitors of HIV reverse transcriptase (RT) are defined.

"Composite Binding Pocket" means the model of the NNI binding site of HIV RT described in copending U.S. patent application Ser. No. 09/040,538.

"Mutant HIV" means a strain of HIV having one or more mutated or altered amino acids as compared with wild type.

"Multi-Drug Resistant HIV" means HIV infection which is resistant to treatment with one or more chemotherapeutic agent.

The Composite NNI Binding Pocket

In the search for subnanomolar NNIs of HIV RT, it was discovered that each reported crystal structure of an RT-NNI complex has a unique binding pattern specific to one chemical class of inhibitors. Considering the limited inhibitor binding knowledge gained from one such structure, it was reasoned that rational drug design efforts should rely on as many crystal structures as possible for maximum design benefit. In this context, it is noteworthy that an analysis of the RT-APA (α-anilinophenylacetamide) structure failed to predict that the chemically dissimilar inhibitor TNK (6-benzyl-1-benzyloxymethyl uracil) could bind in the same region. The RT-APA structure predicts that there would not be enough room in the APA binding site for the 1-benzyloxymethyl group of TNK. Nevertheless, TNK is now known to bind in this region as evidenced by the crystal structure of RT-TNK which shows that RT residues can adjust to accommodate the 1-benzyloxymethyl group.

Conversely, an analysis of the RT-TNK complex does not predict favorable binding of APA in the TNK binding site. The structure does not show how residue E138 could move to accommodate the 2-acetyl group of the α-APA inhibitor. Thus, any NNI binding pocket model based on an individual RT-NNI crystal structure would have limited potential for predicting the binding of new, chemically distinct inhibitors.

Figure 1:
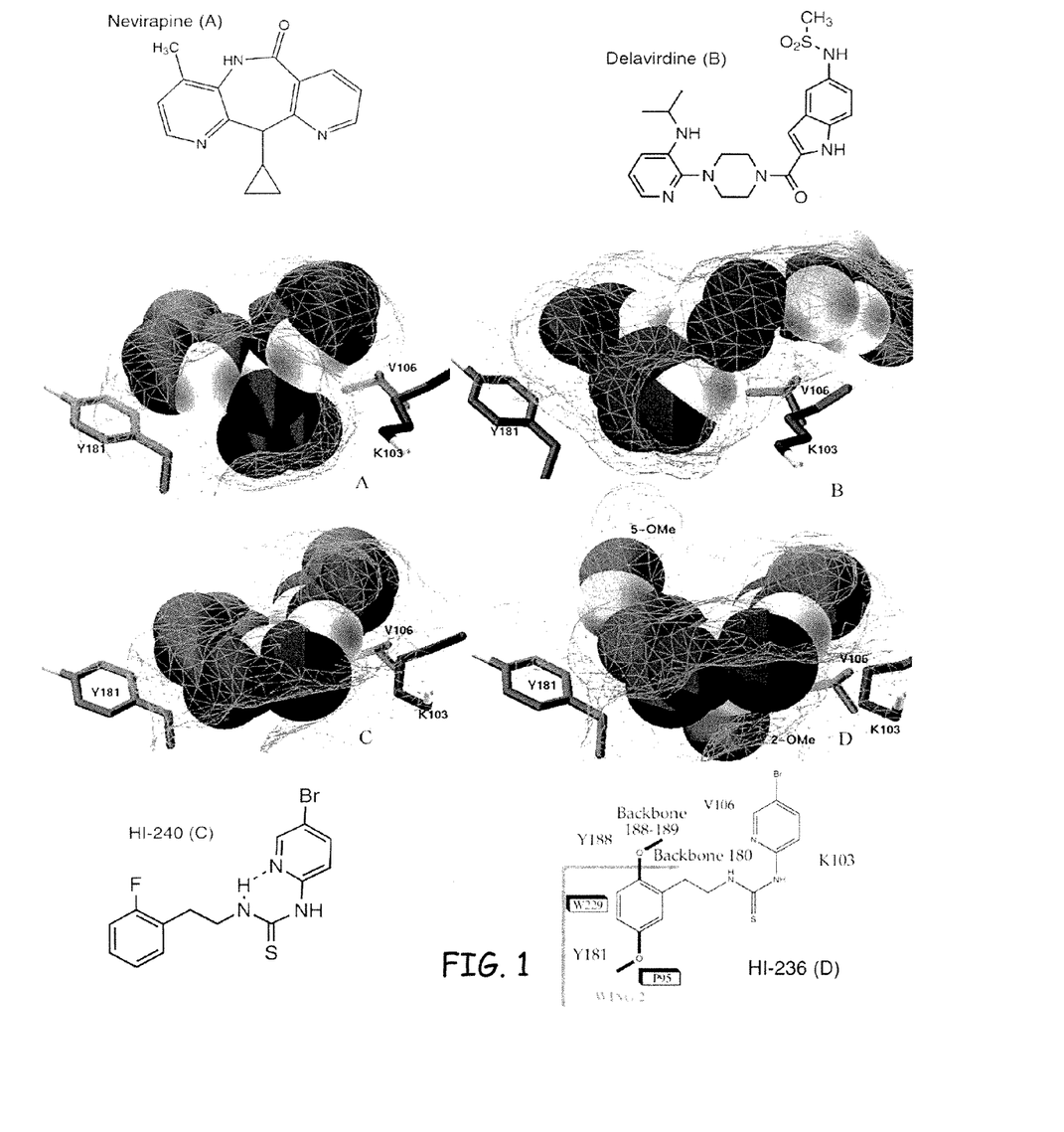
FIG. 1 is a photograph showing inhibitors docked into the NNI binding site of HIV-1 RT, and illustrating how the V106A mutation of RT can decrease the van der Waals contact with the inhibitor. NNIs are shown as stick models. Molecular surfaces of the compounds were prepared and color-coded based on distance calculations between the molecular surface of the NNI binding pocket and the molecular surface of the inhibitor using the GRASP program. Blue indicates the molecular surface is in van der Waals contact with RT residues; yellow indicates the surface area is not in van der Waals contact with RT; red indicates decreased van der Waals contact with RT when V106 is mutated to alanine (MDR RT). Docked molecules include: (A) DDE240; (B) DDE236; (C) DDE280; (D) DDE281; (E) nevirapine; (F) delavirdine; and (G) MKC-422.

To overcome this problem, a method was devised to combine the NNI binding site coordinates of nine RT-NNI crystal structures and to generate a composite molecular surface. The composite model revealed a new NNI binding pocket, as described in copending U.S. patent application Ser. No. 09/040,538. This pocket contains the features not shown or predicted by any of the individual structures alone (FIG. 1).

The composite binding pocket model information showing chemical preference for interactions between inhibitor and binding pocket was implemented to predict favorable interactions (hydrophilic, hydrophobic, hydrogen-bonding) and to facilitate the design of novel inhibitors. The surface of the binding pocket was color-coded accordingly to represent these 3 different regions: hydrophilic, hydrophobic, and hydrogen-bonding regions. As detailed in copending application U.S. patent application Ser. No. 09/040,538, the resulting model, termed the "composite binding pocket model", provided an effective method for selecting favorable substituents on the inhibitor molecules, not only by size but also by chemical nature.

This novel composite binding pocket was used, together with a computer docking procedure and a structure-based semi-empirical score function, as a guide to predict energetically favorable positions of new NNI compounds in the NNI binding site of RT. A number of computational tools were developed, which provided a cogent explanation for the relative activity differences among known compounds and revealed several potential ligand derivatization sites for generating new inhibitors.

Prediction of RT Inhibition Against Drug-resistant Mutants

The modeling studies revealed some important details regarding RT mutations leading to NNI resistance. One observation is that the Wing 2 region of the composite binding pocket consists of multiple aromatic residues including Y181, Y188 and W229. Residues Y181 and Y188 occupy a substantial volume within the binding pocket. Any mutations at Y181 or Y188 would provide a smaller residue in the. Wing 2 region, which is indeed the case for Y181C, Y188C, and Y188H mutations in drug-resistant HIV strains. These mutations occupy a smaller volume of Wing 2, leading to a larger unoccupied volume in the binding pocket. An inhibitor which lacks a compatible functional group to interact with the mutated residues of Y181C, Y188C, and Y188H (a nonpolar group for Y181C and Y188C; and an aromatic group for Y188H) and which lacks a large enough group to provide surface contact with the mutated region, could result in drug resistance. This may explain the poor activity of nevirapine and delavirdine against the Y181C RT mutant (Table 2).

As for other RT mutants, the V106A mutation introduces a smaller aliphatic residue which leads to a slightly larger binding pocket volume in this region. As is the case for the Y181 and Y188 mutants, an inhibitor which does not sufficiently fill the additional volume in the V106A mutant binding pocket with a compatible (hydrophobic) functional group and which does not provide adequate van der Waal's contact with A106 may result in lower activity against the V106A RT mutant. For example, V106A can exhibit reduced van der Waals contact between the linker region located between Wing 1 and Wing 2 and the NNI compound nevirapine or delavirdine. This loss of hydrophobic contact considerably reduces, but does not abolish, the RT inhibitory activity of the NNI (Table 2). Notably, delavirdine was shown to be more potent that nevirapine against all mutants tested and against the wild type RT. Residue K103 of the wild type RT occupies a distinct volume of the binding site and possesses an electrostatic property allowing interaction with DDE192 which may be important for the stabilization of the K101 loop. The K101 loop is in close contact with nevirapine and delavirdine, and any alterations in this region (i.e., the K103N mutation) can cause weaker binding and result in RT resistance to these drugs.

It would be advantageous to maximize the contact between NNI and the Wing 2 residues This can be accomplished by designing inhibitors which incorporate information gained from our composite binding pocket model, including that discussed above. Resulting drugs designed with the modeling information, such as DDE236 and DDE240 have an inherent advantage in their ability to inhibit both wild-type RT as well as RT having mutations at Wing 2 (Table 2).

Designed inhibitors DDE236 and DDE240 were predicted to have significant activity against Wing 2 mutations such as Y191C and YI98C which render most NNIs inactive. In contrast, the V106A mutant is not predicted to effect the RT inhibitory activity of these compounds significantly.

TABLE 1

Modeling Analysis of PETT Compound with Drug-Resistant Mutation of Residues in RT NNI binding Pocket With Side chains Directly Involved in NNI Binding.

| RTNNI | Residue | Drug Mutants | Reduced Activity Mutants | | | |
|---|---|---|---|---|---|---|
| | | | DDE236$^c$ | | DDE240 | |
| Wing 1 | K103 | K103N | −10 fold | Hydrogen | −10 fold | Hydrogen |
| Wing 1 | V106 | V106A | 0 fold | | 0 | |
| Wing 1 | V179 | V179D, E | 0 fold | no change | 0 | No change |
| Wing 1 | P236 | P236L | +4 fold | Hydrophobic | +4 | Hydrophobic |
| Wing 1 | Y318 | No$^a$ | — | — | — | |
| Linker | L100 | L100I | 1.5 fold | Hydrophobic | −1.5 fold | Hydrophobic |
| Linker | L234 | No$^a$ | — | | — | |
| Wing 2 | P95 | No$^a$ | — | | | |
| Wing 2 | Y181 | Y181C, I | — | | — | |
| Wing 2 | Y188 | Y188C, H, LL | 10 fold | Hydrophobic | −35 fold | Hydrophobic |
| Wing 2 | W229 | No$^a$ | 20 fold | Hydrophobic | −50 fold | Hydrophobic 1 |

Referring to Table 1, no NNI-resistant mutation has been reported. Mutants were selected via treatment by Nevirapine, Delavirdine and Efavirenz; Changes in RT inhibition against some RT mutants have been reported and are listed in Table 1. A calculated change of RT inhibition against mutants based on the composite binding pocket model using the same procedure as was applied to the Ki prediction of our designed compounds (docking procedure and modified LUDI score function). The data indicated that the K103N mutation will result in a structural loss in the charge interaction with residue D192; the charge pair is critical to keep the K103-containing loop in place to form a hydrogen bond with NNI. The P236L mutant is unlikely to be selected by DDE236 and DDE240 because of the predicted enhanced inhibition due to the gain of hydrophobic contact (P236L).

It was postulated that the lead compound DDE240: N-[2-(2-fluorophenethyl)]-N'-[2-(5-bromo-pyridyl)]thiourea, (Vig et. al, 1998, *Bioorg & Med. Chem.*, 6:1789) would be effective against HIV RT mutants. DDE240 was predicted to interact more favorably with RT mutants than other compounds such as nevirapine or delavirdine. The activity of DDE24o, which contains a 2'-fluoro group (FIG. 1C) against wild type HIV RT was compared with compounds which contained fluoro substitutions at other positions on the phenyl ring (3'-F and 4° F.). DDE240 was shown to be the most active comound in enzyme assays measuring inhibition of recombinant RT (IC50rRT=0.6 μM), followed by the 3'-F compound DDE241 (IC50rRT=0.76 μM), and lastly, 4'-F, DDE242 (IC50rRT=6.06 μM).

HIV replication assays using peripheral blood mononuclear cells infected with the NNI-sensitive HIV strain HTLV IIIB showed a similar trend, with IC50[p24] values <1 nM for 2'-F (DDE240) and 10 nM for the 4'-F compound. DDE240 was more potent than PETT derivatives DDE253, DDE445, DDE172, and DDE276, and more potent than the S-DABO compounds DDE280 and DDE281 against both wild type RT and MDR RT (see Table 2). The inhibition trend for compounds tested against recombinant wild type RT was consistent with the inhibition trend for MDR RT.

Modeling analysis further revealed that the extensive contact of the V106 residue with the alkylthio group of S-DABO derivatives (DDE280 and DDE281) constitutes additional van der Waals contact which is lost upon mutation to MDR RT. Because the van der Waals contact loss is more pronounced for the S-DABO derivatives for the PETT compounds (DDE240, DDE241, and DDE253), the compounds DDE280 and DDE281 are predicted to have a lower activity against MDR RT. The molecular modeling is consistent with the measured IC50 values, showing relatively poor perfomance of DDE280 and DDE281 against MDR RT (Table 2).

The lead compound, DDE240 was more active than trouviridine (Table 2). Trouviridine was three times less potent than DDE240 against the multiple drug resistant mutant strain of HIV RT (Table 2), which may reflect the fact that trouviridine lacks a polar ring substituent that can provide more favorable interactions with binding site residues. The polar character of the Wing 2 residues of RT that can interact favorably with the 2'-F group of DDE240 in the binding site would be unaffected by the clinically observed mutants K103N, V106A, Y181C DDE240 (see FIG. 1D). Therefore, the favorable interaction of the binding pocket with the 2° F. group of this inhibitor would not be lost in these mutants. In addition, since DDE240 was 100- to 1000-fold more potent than delaviridine or nevirapine against WT RT, a decrease in DDE240 potency against an RT mutant would likely still leave DDE240 as a relatively potent inhibitor, which may not be the case for the inherently less potent compounds such as nevirapine and delaviridine.

Modeling analysis indicated the Y181 residue stacks in a favorable herringbone orientation with the aromatic residue of NNI compounds such as DDE240. The Y181 stacking interaction is lost in the Y181C mutant, which is predictive of some degree of resistance against DDE240, delaviridine, and nevirapine. The activity of DDE240 against the Y181C mutant was 200-times better (IC50=0.2 μM) than delavirdine (IC50=50 μM), and more than 500 times more potent than nevirapine (IC50>100 μM).

The MDR mutant strain contains one mutation, V106A, which is located in the NNI binding pocket. Because delaviridine, nevirapine, and DDE240 all have a central portion of the molecule which is in contact with RT residue 106, they appear to show comparably lower activities against this mutant. However, the degree of resistance differed for the three compounds. DDE240 showed 100-fold better activity (IC50 μM=0.006 μM) against MDR HIV than delavirdine (0.4 μM) and an 800 fold better activity than nevirapine (5 μM).

Analysis of the fit of the NNI and other inhibitors in the composite binding pocket demonstrated that the Wing 2 region has substantial molecular volume (approximately 160 cubic angstroms) surrounding the phenyl ring, defining a space that could potentially be more efficiently occupied with a larger functional group. Novel thiourea compounds were designed to optimize van der Waals contact with the binding pocket, predicting improved potency against WT RT and improved inhibition profile against Wing 2 mutants of RT. DDE236 was synthezized as a compound with one methoxy group at the 2' position (same as the fluoro atom of DDE240) and a second methoxy group at the 5' position of the phenyl ring which can contact the Wing 2 region (see FIG. 1B).

Analysis of the docking of DDE236 in the NNI binding site showed that the unoccupied volume with this inhibitor was 135 cubic angstroms, a decrease of 25 cubic angstroms relative to the unoccupied volume surrounding DDE240. (See FIGS. 1C–1D). These docking results are consistent with the activity data showing an improved potency for DDE236, correlating to improved contact with the binding site residues.

Table 2: Inhibitory Activity of DDE236 and DDE240 on p24 Production in Peripheral Mononuclear Cells Infected with HIV Strains HTLV-IIB, RT-MDR, A17, and A17 Variant.

TABLE 2

Inhibitory activity of DDE236 and DDE240 on p24 production in peripheral mononuclear cells infected with HIV strains HTLV-IIIB, RT-MDR, A17, and A17 variant.

| RT Inhibitors | RRT (μM) | HTLV IIIB WT IC50 p24 (μM) | RT-MDR (74V, 41L, 106A, 215Y) IC50 p24 (μM) | A17 (Y181C) IC50 p24 (μM) | A17 variant (Y181C, K103N) IC50 p24 (μM) |
|---|---|---|---|---|---|
| DDE236 | 0.1 | <0.001 | 0.005 | 0.1 | 11 |
| DDE240 | 0.6 | <0.001 | 0.005 | 0.2 | 41 |
| DDE241 | 0.7 | <0.001 | 0.02 | N.D. | N.D. |
| DDE242 | 6.4 | N.D. | N.D. | N.D. | N.D. |
| DDE253 | 0.7 | <0.001 | 0.004 | N.D. | N.D. |
| DDE245 | 3.7 | 0.003 | N.D. | N.D. | N.D. |

TABLE 2-continued

Inhibitory activity of DDE236 and DDE240 on p24 production in peripheral mononuclear cells infected with HIV strains HTLV-IIIB, RT-MDR, A17, and A17 variant.

| RT Inhibitors | RRT ($\mu$M) | HTLV IIIB WT IC50 p24 ($\mu$M) | RT-MDR (74V, 41L, 106A, 215Y) IC50 p24 ($\mu$M) | A17 (Y181C) IC50 p24 ($\mu$M) | A17 variant (Y181C, K103N) IC50 p24 ($\mu$M) |
|---|---|---|---|---|---|
| DDE172 | 5.8 | <0.001 | >1 | N.D. | N.D. |
| DDE276 | >10 | 3.8 | >1 | N.D. | N.D. |
| DDE280 | 5.6 | <0.001 | 28 | >100 | >100 |
| DDE281 | 7.0 | 0.016 | 7 | 38 | 55 |
| Delavirdine | 1.5 | 0.009 | 0.4 | 50 | >100 |
| Nevirapine | 23 | 0.034 | 5 | >100 | >100 |
| MKC-442 | 0.8 | 0.004 | 0.3 | N.D. | N.D. |
| Trovirdine | 0.8 | 0.007 | 0.02 | N.D. | N.D. |
| AZT | N.D. | 0.004 | 0.15 | 0.006 | 0.004 |

N.D. = not determined;
WT 32 wild type.

The synthesis of DDE172, DDE240, DDE241, DDE253, DDE280; and DDE281 and their activites against WT RT expressing the HTLV IIIB strain of HIV-1 was previously reported (Vig et. al, 1998, *Bioorg & Med. Chem.*, 6:1789; Sudbeck et. al., 1998, *Antimicro. Agents & Chemotherapy*, 42:3225; and Vig et. al., 1998, *Bioog & Med. Chem. Lett.* 8:1461).

Design and Modeling Analysis of DDE236

A computer simulation of the binding of DDE236 into the NNI binding site of RT was accomplished using a molecular docking procedure. Docking of these compound into the NNI binding site required the use of X-ray coordinates of an RT/NNI complex (in this case the RT/9CL-TIBO complex). Upon binding to RT, the compound can fit into a butterfly-shaped NNI binding site (described by Ding et. al., 1995, *Nat. Struct. Biolog.* 11:1122 (FIGS. 1A and 2A) Once the final docked position of the molecule in the NNI site was determined, the molecule was assigned a score, from which an estimation of the inhibition constant (Ki. value) was determined. When trovirdine was docked into the NNI binding site of RT it had a higher binding score than PETT and fit into the butterflyshaped binding region with one part residing in Wing I and the other in Wing 2. The ring closest to the thiocarbonyl group resided near the Lys(K) 101 loop and the other pyridyl ring was near Trp(W)229.

After docking and Ki. estimation was completed for the trovirdine, evaluation of the docked compounds in the active site of RT involved placing each compound into the composite binding pocket using the same orientation matrix utilized in its construction. The potentially flexible regions in the binding site were then readily identified as were atom sites for future derivatization of the compounds. The area within Wing 2 and the residues near the thiourea group seemed to be the most forgiving regions in the binding site of RT. It was postulated that a more efficient use of such sterically allowed unoccupied spatial gaps in the binding site could be achieved by replacing the 2-pyridyl ring of trovirdine with a 2,5-dimethoxyphenyl moiety (DDE236) and yield potentially more active PETT compounds with larger molecular surface areas, higher Ludi scores, and lower Ki. values.

The molecular surface area of the compounds after docking was calculated. At docked positions, the atom surface area in contact with the protein residues constituted an average of 84% of the entire molecular surface. We used this average value in the calculation of the inhibitory constant (ki.) based on the Ludi score function. The calculated Ki. value of DDE236 (0.2 $\mu$M) was better than those of known compounds PETT (2.4 $\mu$M) and trovirdine (0.7 $\mu$M).

The docking studies indicated that the 2-methoxy group of DDE236 is situated beneath the ethyl linker and fits favorably into a cavity of the binding pocket, providing contact with protein residues that cannot be achieved by trovirdine. Likewise, the 5-methoxy group of DDE236 provides close contact with residues Pro95 and Trp229. The trend of the calculated Ki values appeared to predict the trend of the experimentally determined IC50 values from HIV replication assays (Table 2). The compound DDE236 with the lowest calculated Ki values of the series was 8-times more potent than trovirdine against purified recombinant HIV-RT using the cell-free Quan-T-RT system (IC50 [rRT] was 0.1 $\mu$M for DDE236 versus 0.8 $\mu$M for trovirdine). DDE236 also elicited potent anti-HIV activity with IC50 values of less than 0.001 $\mu$M in 3 of 3 independent experiments which was consistently lower than the IC50 values for trovirdine (0.007 $\mu$M) and AZT (0.004 $\mu$M). Furthermore, the IC90 value of our DDE236 (9 nM) was 10-fold better than that of AZT (100 nM). None of the PETT derivatives were cytotoxic at concentrations as high as 100 $\mu$M. Therefore, the calculated selectivity index (IC50 [MTA] IC50[p241) of DDE236 was >$10^5$.

The same modeling procedure was applied to RT mutants (Table 1). DDE236 was predicted to have better Ki value than the trovirdine against the RT mutants examined (Table 2) for the following reasons. DDE236, which contain larger functional group which can contact the Wing 2 region of RT (based on our composite binding pocket model) will not only have significant potency against wild-type RT but will also show high potency against many RT mutants such as Y181 C which is resistant to many examined NNI inhibitors currently in clinical use.

Design and, Modeling Analysis of DDE240

Similar to the design of DDE236, the design of DDE240 was also focused on improving its interaction with the Wing 2 region. However, instead of using large group to better contact with binding pocket, the fluoro atom was used to improve the contact with the binding pocket based on compatible chemical nature. The position of the docked trovirdine molecule revealed multiple potential derivatization sites for incorporation of polar groups, at specific locations. The favorable regions for polar groups were readily identified by blue color-coding on the surface of the binding pocket model. The 3'-position on the pyridyl ring of trovirdine (equivalent to the ortho or C2 position of a phenyl derivative) would be a good location for a fluorine atom because it could interact favorably with nearby polar residues in the composite binding pocket (FIG. 1). The 5' position on the pyridyl ring (para or C4 position of a phenyl derivative) of trovirdine would be near a hydrophobic region however, making it a poor location for a fluorine substituent. DDE240 with fluoro substituent at ortho position on the ring was synthesized and tested for anti-HIV activities.

Coordinates of DDE240 were generated and positioned into the crystal structure coordinates of the RT/9-C1-TIBO active site by a docking procedure (Methods) identical to that used for DDE236. The main conformational difference between the energy-minimized model of DDE240 and its crystal structure is a 120° rotation around the ethyl linker, which could be stabilized by favorable contacts with binding site residues if the molecule adopted this conformation upon binding. This conformation of the energy-minimized model of DDE240, aided by an intramolecular hydrogen, allows the molecule to fit favorably into the NNI bond (also observed in the crystal structure o binding site of RT.

After the molecules were docked into the binding site, an assessment of how well they would be predicted to bind was done. The color-coded composite binding pocket illustrating preferred regions of interaction shows that Wing 2 is mostly hydrophobic except for the region near the ortho positions of the phenyl ring of the inhibitor, where a polar group such as fluorine would be compatible. Substitutions at the meta position would be on the edge between the polar region and the hydrophobic region of the binding site. Modeling of DDE240 showed that the ortho-F group does interact favorably with the polar region of the binding site, which would contribute to a stronger binding to RT. The ortho-F group was predicted to be located near the interface between polar and hydrophobic regions of the binding site, where the meta-F substituent is half exposed to the polar (blue) region. This suggests that the meta-F group could interact favorably with the polar region only if the fluorine is in the correct orientation. If the orientation of the meta-F group was such that it would extend toward the hydrophobic region instead, weaker binding would result. The para-F group was apparently not compatible with the composite binding pocket.

The ortho-F substituted compound DDE240 was shown to be the most active in enzyme assays measuring inhibition of recombinant RT (IC50rRT=0.4 µM), followed by meta-F (IC5OrRT 0.7 µM), and lastly para-F (IC50rRT=6.O µM). The HIV replication assays using peripheral blood mononuclear cells infected with the zidovudine-sensitive HIV strain HTLVHM showed a similar trend, with IC50[p24] values <1 nM for o-F DDE240 and 10 nM for the p-F compound. The para-F atom, which is small in size but electronegative, is probably compatible with the location of the ring plane of nearby hydrophobic Trp229 but offers an interaction less favorable than that of o-F or m-F. Trovirdine was shown to be 10 times less potent than DDE240 against the zidovudine-sensitive HIV strain HTLVM and up to 7 times less potent than DDE240 against the multiple-drug-resistant mutant strain of HIV RT (Table 2), which may reflect the fact that trovirdine lacks a polar ring substituent which can provide more favorable interactions with binding site residues.

EXAMPLES

Methods

Construction of the NNI Binding Pocket

Modeling studies required the construction of a binding pocket which encompassed all RT-NNI complexes with known crystal structures. First, a total of eight coordinates of RT complexes with the compounds HEPT, MKC, TNK, APA, Nevirapine, N-ethyl Nevirapine derivative, 9-C1 TIBO (Stuart et al.),22 and 9-C1 TIBO with PDB access codes rti, rt1, rt2, hni, vrt, rth, rev and tvr, respectively, were superimposed onto the full coordinates of RT complexed with 8-C1TIBO (PDB access code hnv). The "thumb" region of RT complexes are relatively variable compared with the palm region. Therefore, a total of 1 17 Cα atoms of the residues from 97 to 213 which cover part of the NNI binding site and the palm region were used for a least-squares superimposing procedure within the program. The RMS values are shown to be 1.00, 0.98, 0.99, 0.62, 0.80, 0.87, 0.94 and 0.65 k for HEPT, MKC, TNK, APA, Nevirapine, N-ethyl nevirapine derivative and two 9-C1 TIBO complexes, respectively. The coordinates of the corresponding inhibitor molecules were then transformed according to the same matrices derived from the superimposition. Lastly, an overall molecular surface providing a binding pocket encompassing all inhibitors was generated from the overlaid non-hydrogen atom coordinates of all inhibitors using the program GRASP. The surface of the binding pocket was color-coded to reflect characteristics of the overlaid inhibitors, such as hydrogen bonding, hydrophilic, and hydrophobic regions. The nitrogens on the uracil ring of HEPT and TIBO derivatives were color coded red for hydrogen-bonding atoms. Oxygen or sulfur atoms of carbonyl, thiocarbonyl, and ester groups, nitrogen atoms of amine groups, and halogen atoms were color-coded blue for polar (hydrophilic) groups. Carbon atoms were considered to be hydrophobic and were colored gray. This pocket, referred to as the composite binding pocket, was used as a basis for the analysis of inhibitor binding to the NNI binding site of HIV RT.

Docking and K, Prediction

Fixed docking in the Affinity program within as used for docking small molecules to the NNI binding site which was taken from a crystal structure (PDB code rev, RT/9-C1-TIBO complex). The program has the ability to define a radius of residues within a 5A distance from the NNI molecule. As the modeling calculations progressed, the residues within the defined radius were allowed to move in accordance with energy minimization. Ten final docked positions were initially chosen for each inhibitor modeling calculation but failed to reveal more than two promising positions. Later, only two calculated positions were set for the search target. Calculations were carried out on a SGI INIDIG02 using the CVFF force field in the Discover program and a Monte Carlo search strategy in Affinity. No salvation procedures were used. Since the total number of movable atoms exceeded 200, conjugated gradient minimization was used instead of the Newton minimization method. The initial coordinates of the compounds were generated using the Sketcher module within InsightII. Each final docking position was then evaluated by a score function in Ludi. The top scoring model was then compared with the composite binding pocket and the known crystal structure of similar compounds and used for further analyses.

Several modifications were imposed during the calculation of inhibitory constants (ki) of the positioned compounds using the Ludi score function. First, the molecular surface areas (MS) were directly calculated from the coordinates of the compounds in docked conformations using the MS program. Second, we re-evaluated the number of rotatable bonds (NR) which was assessed inaccurately by INSIGHTII (rigidity imposed by hydrogen bonding was not accounted for in the program). Third, we assumed that the conserved hydrogen bond with RT did not deviate significantly from the ideal geometry. This assumption was supported by the fact that in the known crystal structures of RT complexes, all hydrogen bonds between NNIs and RT are near the ideal geometry. Lastly, for the trovirdine compounds, we found it necessary to impose an additional penalty for a charged group or halogen atoms when positioned near the ring plane of a protein residue such as tryptophan 229 because the interaction was not adequately accounted for in the Ludi score. The working modification of the Ludi scoring function for the PETT compounds included subtracting a score of P from the total Ludi score when the ring plane of the Trp229 was within 5 A distance from a para substituent (R):

Ludi Score=$MS*BS.2.93+95$ (H-bond)$-NR*24.2-100-P$;

Where
P=200, when R=a hydrophilic group, e.g. —OH or —NO2;
P=100, when R=a para-halo atom, e.g. —F, —Cl or —Br;
P=50, when R=a para-methoxy, e.g. —OMe;
P=O, when R=a hydrophobic group, e.g. H, CH3;

Consequently, the Ki values for the modeled compounds were more predictable than they would be otherwise without such modification.

Chemistry

All chemicals were purchased from the Aldrich Chemical Company (Milwaukee, YM. Anhydrous acetonitrile and N,N-dimethylformaniide were obtained from Aldrich in sure seal bottles and were transferred to reaction vessels via cannula under nitrogen. All reactions were carried out under the atmosphere of nitrogen. Nuclear magnetic resonance (NMR) spectra were recorded on a Varian 300 MHz instrument and chemical shifts are reported in parts per million (ppm) relative to tetramethyl silane as an internal standard. Splitting patterns are designated as follows: s=singlet, d=doublet, t=triplet, q=quartet, m=multiplet, br=broad peak. C NMR spectra were recorded in CDC13 on the same instrument using the proton decoupling technique. The chemical shifts reported for 14C NMR are referenced to chloroform at 77.0 ppm. NMR spectra were recorded in CDC13 and a 1% solution of trifluroacetic acid in water was used as an internal standard in a fused capillary tube.

Melting points were obtained using a Fisher-Johns melting apparatus and are uncorrected. UV spectra were recorded from a Beckmann Model # DU 7400 UVN is spectrometer using a cell path length of 1 cm. Fourier transform infrared spectra were recorded using an FF-Nicolet model Protege #460 instrument. Mass spectra analysis were conducted using a Hewlett-Packard Matrix Assisted Laser Desorption Time-of-Flight (MALDI-TOF) spectrometer model # G2025A. The matrix used was cyanohydroxycinnamic acid. Column chromatography was performed using EM Science silica gel 60. The solvents used for elution varied depending on the compound and included one of the following: ethyl acetate, methanol, chloroform, hexane, methylene chloride or ether. Elemental analysis was performed by Atlantic Microlabs (Norcross, Ga.).

N-[2-(2,5-dimethoxyphenylethyl)]-N'-[2-(5-bromopyridyl)]-thiourea (DDE236) white solid (2 g, 67%); mp 133–138° C.; UV (MEOH) $\lambda$max: 202, 205, 231, 276 and 300 nm; IR(KBR Disc) v 3209, 3152, 3078, 3028, 2951, 2831, 1595, 1533, 1468, 1306, 1227, 1095, 1059, 1022, 862, 825, 796, 707 cm$^{-1}$; $^3$H NMR(CDCl$_3$) $\delta$ 11.24 (br s, 1H), 9.30 (br s, 1H), 8.10–8.09 (d, 1H), 7.65 (dd, 1H), 6.82–6.76 (m, 4H), 4.03–3.97 (q, 2H), 3.77 (s, 3H), 3.76 (s, 3H), 3.00–2.96 (t, 2H); $^{14}$C NMR(CDCl$_3$) $\delta$ 178.7, 153.1, 151.8, 151.7, 146.5, 140.9, 128.1, 117.7, 113.3, 112.6, 111.2, 110.9, 55.7, 55.5, 45.6, and 29.9; MALDI-TOF mass found, 394.0 (M−1), 396.0 (M+1), calculated, 395.0; Anal. (Cl$_6$H$_{18}$BrN$_3$O$_2$S)C, H, N, S, Br.

N-[2-(2-fluorophenethyl)]-N'-[2-(5-bromopyridyl)]-thiourea (DDE240)

yield: 7 1%; mp 156–157° C.; UV (MeOH) $\lambda$max: 209, 256, 274 and 305 nm; IR(KBr) v 3446, 3234, 3163, 3055, 2935, 1672, 1595, 1560, 1531, 1466, 1390, 1362, 1311, 1265, 1227, 1169, 1136, 1089, 1003, 864, 825, 756 cm$^{-1}$; $^1$H NMR (CDCl$_3$) $\delta$ 11.36 (br s, 1H), 9.47 (br s, 1H), 8.05–8.04 (d, 1H), 7.72–7.68(dd, 1H), 7.30–7.03 (m, 4H), 6.87–6.84 (d, 1H), 4.06–3.99 (q, 2H), 3.10–3.05 (t, 2H); $^{14}$C NMR (CDCl$_3$) $\delta$ 179.1, 163.1, 151.7, 146.2, 141.1, 131.2, 131.1, 128.5, 128.4, 124.1, 115.5, 115.2, 113.6, 112.2, 45.8 and 28.2; $^{19}$F NMR(CDC13) 8–42.58 & 42.55 (d); Maldi Tof found: 355.0 (M+I), calculated: 354.0; Anal. (C$_{14}$H$_{13}$BrFN$_3$S)C, H, N, S.

General Procedure for Synthesis

Compounds were synthesized according to Scheme 1. In brief, 2-amino-5-bromopyridine was condensed with 1,I-thiocarbonyl diiniidazole to fumish the precursor thiocarbonyl derivative (A). Further reaction with appropriately substituted phenylethyl amine gave the target PETT derivatives in good yields.

Specifically, thiocarbonyldiiniidazole (8.90 g, 50 mmol) and 2-amino-5-bromo pyridine (8.92 g, 50 mmol) were added to 50 mL of dry acetonitlile at room temperature. The reaction mixture was stirred for 12 h and the precipitate filtered, washed with cold acetonitrile (2×25 mL), and dried under vacuum to afford (I 1.40 g, 80%) of compound A. To a suspension of compound A (0.55 eqv) in dimethyl formamide (15 mL) an appropriate amine (0.50 eqv) was added. The reaction mixture was heated to IOO'C. and stiffed for 15 h. The reaction mixture was poured into ice-cold water and the suspension was stirred for 30 min. The product was filtered, washed with water, dried, and further purified by column chromatography to furnish the target compounds 1–9 in good yields.

Purified RT Assays for Anti-HIV Activity

Compounds 3a–3d were tested for RT inhibitory activity (IC50[rRT]) against purified recombinant HIV RT using the cell-free Quan-T-RT system (Amersham, Arlington Heights, Ill.), which utilizes the scintillation proximity assay principle.38 In the assay, a DNA/RNA template is bound to SPA beads via a biotin/strepavidin linkage. The primer DNA is a 16-mer oligo(T) which has been annealed to a poly(A) template. The primer/template is bound to a strepavidin-coated SPA bead.

3H-TTP is incorporated into the primer by reverse transcription. In brief, 3H-TTP, at a final concentration of 0.5 μCi/sample was diluted in RT assay buffer (49.5 mM Tris-Cl, pH 8.0, 80 mM KCl, 10 MM $MgCl_2$ 10 mM DTT, 2.5 mM EGTA, 0.05% Nonidet-P-40), and added to annealed DNA/RNA bound to SPA beads. The compound being tested was added to the reaction mixture at 0.001 μM–100 μM concentrations. Addition of 10 mU of recombinant HIV RT and incubation at 37'C for 1 hour resulted in the extension of the primer by incorporation of 3 H-TFP. The reaction was stopped by addition of 0.2 ml of 120 mM EDTA. The samples were counted in an open window using a Beckman LS 7600 instrument and IC, values were calculated by comparing the measurements to untreated samples.

Reagents and conditions: i) 1,1-thiocarbonyldiimidazole, acetonitrile, RT, 12 h.
ii) DMF, Ph-$CH_2$-$CH_2$-$NH_3$, 100° C., 15 h p24 Assays for Anti-HIV Activity Normal human peripheral blood mononuclear cells (PB-MNC) from HIV-negative donors were cultured 72 hours in RPMI 1640 supplemented with 20% (v/v) heat-inactivated fetal bovine serum (FBS), 3% interleukin-2, 2 mM L-glutairtine, 25 mM HEPES, 2 μL, NAHCO, 50 mg/mL gentamicin, and 4 μg/mL phytohemagglutinin prior to exposure to HIV-I at a multiplicity of infection (MOI) of 0.1 during a one-hour adsorption period at 37'C in a humidified 5% C02 atmosphere. Subsequently, cells were cultured in 96-well microliter plates (100 μl/well; 2×106 cells/mL, triplicate wells) in the presence of various inhibitor concentrations and aliquots of culture supernatants were removed from the wells on the 7th day after infection for p24 antigen p24 enzyme immunoassays (EIA), as previously described. (see Erice et. al., 1993, *Antiimicrob. Ag. Chemotherapy* 37:835–838) The applied p24 EIA was the unmodified kinetic assay commercially available from Coulter Corporation/Immunotech, Inc. (Westbrooke, Me.), which utilizes a murine monoclonal antibody to HIV core protein coated onto microwell strips to which the antigen present in the test culture supernatant samples binds. Percent inhibition of viral replication was calculated by comparing the p24 values from the test substance treated infected cells with p24 values from untreated infected cells (i.e., virus controls). In parallel, the effects of various treatments on cell viability were also examined, as described in Enrice et. al., supra. In brief, non-infected PBNWC were treated with each compound for 7 days under identical experimental conditions. A Microculture Tetrazolium Assay (NTFA), using 2,3-bis(2-methoxy-4 nitro-5-sulfophenyl)-5-[(phenylamino)-carbonyl]-2H-tetrazolium hydroxide (XTT), was performed to quantitate cellular proliferation.

CONCLUSIONS

Novel molecules DDE236 and DDE240, namely N-[2-(2,5-dimethoxyphenylethyl)]-N'-2-(5-bromopyridyl)]-thiourea and N-[2-(2-fluorophenylethyl)]-N'-[2(5-bromopyridyl)]-thiourea have been designed. These compounds exhibit unprecedented picomolar potency against HIV RT wild-type and drug-resistant mutants (Table 2). The design strategy was based on taking full advantage of the previously identified space in the composite binding pocket model and modeling of clinically identified mutation in the NNI binding pocket. These NNI compounds exhibit anti-HIV activity superior to that of the parent compounds and are more effective against drug-resistant strains of HIV.

This specification makes reference to numerous patent and literature citations, each of which is hereby incorporated by reference for all purposes as if fully set forth in the text.

I claim:

1. A method for inhibiting replication of a virus of an HIV strain that is resistant to a chemotherapeutic agent, the method comprising:

contacting the resistant virus with an amount of a compound effective to inhibit replication of the virus, wherein the compound is of the formula:

wherein x is: 2,5-OMe or o-F.

2. The method of claim 1, wherein the chemotherapeutic agent is Delavirdine, Nevirapine, Efavirenz, Trovirdine, AZT, or MKC-442.

3. A method for inhibiting replication of an HIV having a mutation of an amino acid at position 106 or 183 of reverse transcriptase, the method comprising:

contacting the HIV with an amount of a compound effective to inhibit replication of the HIV, wherein the compound is of the formula:

wherein x is: 2,5-OMe or o-F.

4. A method for inhibiting replication of an HIV having one or more of the following amino acid substitutions in reverse transcriptase: L100I, K103N, V106A, E138K, Y181C, or Y188H; the method comprising:

contacting the HIV with an amount of a compound effective to inhibit replication of the HIV, wherein the compound is of the formula:

wherein x is: 2,5-OMe or o-F.

5. A method for inhibiting replication of a virus of an HIV strain that is resistant to a non-nucleoside inhibitor-resistant strain of HIV; the method comprising contacting the resistant virus with an amount of a compound effective to inhibit replication of the virus, wherein the compound is of the formula:

wherein x is: 2,5-OMe or o-F.

6. A method of inhibiting replication of a virus of an HIV strain selected from the group consisting of RT-MDR, HIV A17, and HIV A17 variant; the method comprising:

contacting the virus with an amount of a compound effective to inhibit replication of the virus wherein the compound is of the formula:

wherein x is: 2,5-OMe or o-F.

7. The method of claim 1, wherein the compound is

8. The method of claim 3, wherein the compound is

9. The method of claim 4, wherein said compound is

10. The method of claim 5, wherein the compound is

11. The method of claim 6, wherein the compound is

12. The method of claim 1, wherein said compound is

13. The method of claim 3, wherein the compound is

14. The method of claim 4, wherein the compound is

15. The method of claim 5, wherein the compound is

16. The method of claim 6, wherein the compound is

17. The method of claim 1, wherein the replication of the virus is inhibited within a human peripheral blood mononuclear cell.

18. The method of claim 2, wherein the replication of the virus is inhibited within a human peripheral blood mononuclear cell.

19. The method of claim 3, wherein the replication of the HIV is inhibited within a human peripheral blood mononuclear cell.

20. The method of claim 4, wherein the replication of the HIV is inhibited within a human peripheral blood mononuclear cell.

21. The method of claim 5, wherein the replication of the virus is inhibited within a human peripheral blood mononuclear cell.

22. The method of claim 6, wherein the replication of the virus is inhibited within a human peripheral blood mononuclear cell.

* * * * *